United States Patent [19]

Kosswig et al.

[11] 4,302,349

[45] Nov. 24, 1981

[54] ADDUCTS OF ALCOHOLS AND OLEFIN OXIDES, SUITABLE FOR REDUCING THE INTERFACIAL SURFACE TENSION OF OILY PHASES WITH RESPECT TO WATER

[75] Inventors: Kurt Kosswig; Ekkehard Wienhoefer, both of Marl, Fed. Rep. of Germany

[73] Assignee: Chemische Werke Huls, A.G., Marl, Fed. Rep. of Germany

[21] Appl. No.: 146,986

[22] Filed: May 5, 1980

[30] Foreign Application Priority Data

Jun. 26, 1979 [DE] Fed. Rep. of Germany ....... 2925628

[51] Int. Cl.$^3$ ..................... C07C 41/04; C07C 43/10; C07C 43/20; C11D 1/722
[52] U.S. Cl. ............................ 252/174.21; 252/52 A; 252/135; 252/156; 252/174.14; 252/351; 252/358; 252/52 R; 568/607; 568/608; 568/624; 568/625
[58] Field of Search ................ 568/624, 625, 608, 607; 252/174.21, 52 A, 59, 135, 156, 174.14, 351, 358

[56] References Cited

U.S. PATENT DOCUMENTS

| | | | |
|---|---|---|---|
| 2,903,485 | 9/1959 | Lane et al. ................ | 252/174.21 X |
| 3,029,216 | 4/1962 | Bailey et al. ................ | 568/625 X |
| 3,240,819 | 3/1966 | Gaertner et al. ................ | 568/623 |
| 3,340,309 | 9/1967 | Weipert ................ | 568/625 |

OTHER PUBLICATIONS

Schoenfeldt, *Surface Active Ethylene Oxide Adducts*, Pergamon Press, Oxford, 1969, pp. 659 et seq.

*Primary Examiner*—Dennis L. Albrecht
*Attorney, Agent, or Firm*—Millen & White

[57] ABSTRACT

Compounds of the following formula are suitable for reducing the interfacial surface tension of oily phases with respect to water:

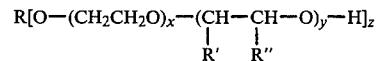

wherein
  z is 1 or 2,
  R, for z=1, is alkyl, aralkyl, or alkylaryl of 8–22 carbon atoms in the alkyl chain, or hydroxyalkyl of 2–22 carbon atoms, and, for z=2, is (aryl)alkylene of 4–18 carbon atoms,
  R' and R" each independently is hydrogen or $C_1$–$C_{20}$-alkyl wherein R' and R" are not simultaneously hydrogen and R' and R" together have 8–20 total carbon atoms,
  x is 10–40 and
  y is 1.2–5.

11 Claims, No Drawings

ADDUCTS OF ALCOHOLS AND OLEFIN OXIDES, SUITABLE FOR REDUCING THE INTERFACIAL SURFACE TENSION OF OILY PHASES WITH RESPECT TO WATER

CROSS REFERENCE TO RELATED APPLICATIONS

This application is related to copending application Ser. No. 146,918, filed on even date.

BACKGROUND OF THE INVENTION

It is known that polyethoxylated fatty alcohols and alkyl phenols are suitable for use as detergents and emulsifiers. In some applications, such as, for example, automatic dishwashers and washing machines, however, the strong foaming capacity of these compounds is a troublesome feature. Attempts have been made to counteract this undesirable property by adding suitable components, such as, for example, higher alcohols or block polymers of polypropylene glycol and ethylene oxide.

Another approach is to modify the hydrophilic portion of the tenside molecule. The replacement of the hydrogen of the terminal hydroxy group by a hydrophobic moiety, although accompanied by reduced water solubility of the resultant compound, produces a markedly reduced foaming tendency in comparison with that of the starting compound which is not "blocked". The complete absence of a terminal hydroxy group additionally causes the resultant compound to exhibit an improved stability in the presence of alkali hydroxides, silicates, or phosphates, i.e., compounds which are mixed with the mentioned tensides, for example, when used in powder-type dishwashing detergents. The literature discloses a plurality of suitable such blocking groups (N. Schoenfeldt, Surface Active Ethylene Oxide Adducts, Pergamon Press, Oxford [1969]: 659 et seq.). Propylene oxide and butylene oxide, in particular, are mentioned most frequently, but styrene oxide and benzyl chloride are also disclosed. Among the hydrophobic moieties enhancing alkali stability are, in particular, isopropyl and tert-butyl, obtainable by acid-catalyzed addition of propene (DAS [German Published Application] No. 2,544,569) or isobutene (DOS [German Unexamined Laid-Open Application] No. 2,556,499) to the end-positioned hydroxy function of the aforementioned tensides. U.S. Pat. No. 2,903,485 discloses the addition product of an epoxyoctane which is not exactly defined ("octylene oxide") to ethoxylated alkyl phenol in a molar ratio of 1:1 as being useful as a low-foaming detergent, especially for automatic dishwashers.

SUMMARY OF THE INVENTION

It is an object of this invention to provide new compounds which are free from the foregoing defects.

Upon further study of the specification and appended claims, further objects and advantages of this invention will become apparent to those skilled in the art.

In one aspect of this invention, these objects have been achieved by providing compounds suitable for reducing the interfacial surface tension of oily phases with respect to water in low concentration, of the formula

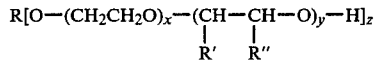

wherein z is 1 or 2,

R is, for z=1, alkyl, aralkyl or alkylaryl of 8–22 carbon atoms in the alkyl chain or hydroxyalkyl of 2–22 carbon atoms, and, for z=2, (aryl)alkylene of 4–18 carbon atoms in the alkyl chain, R' and R" each independently is hydrogen or $C_1$–$C_{20}$-alkyl wherein R' and R" are not simultaneously hydrogen and R' and R" together have a total of 8–20 carbon atoms, x is 10–40 and y is 1.2–5.

DETAILED DISCUSSION

The compounds of this invention can be prepared, e.g. by reacting a compound $R(OH)_z$ in the presence of a basic or acidic catalyst first with ethylene oxide and then with an epoxyalkane of the formula

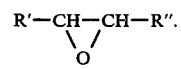

That is, these compounds can be produced by the base- or acid-catalyzed addition of more than 1 mole of alkane epoxide of 10–22 carbon atoms to oxyethylates of compounds having active hydrogen, such as alkyl phenols and especially alcohols of the same carbon atom range.

Moieties R in the formula of the compounds of this invention include those mentioned below in conjunction with starting materials $R(OH)_z$.

Suitable compounds $R(OH)_z$ for use in the process of this invention include, therefore, those to which ethylene oxide can be added in the presence of a suitable conventional basic or acidic catalyst. Included among such compounds are straight-chain or branched, optionally substituted, (e.g., by methoxy-, cyano-, nitro, fluoro, or chloro) primary and secondary alcohols, straight-chain and branched 1,2-, 1,3-, and α,ω-alkanediols, aryl alcohols, arylalkyl diols and alkyl phenols.

Suitable compounds of this type include, for example, 1-octanol, 2-octanol, 1-decanol, 1-undecanol, 2-undecanol, 1-dodecanol, 1-tridecanol, 2-tridecanol, 1-tetradecanol, 1-hexadecanol, 1-octadecanol, 1-eicosanol, 1-docosanol, 2-ethylhexanol, etc.; mixtures of alcohols of natural origin (prepared by hydrogenation of vegetable or animal fats); alcohols prepared in the Ziegler synthesis and subsequent oxidation, or mixtures thereof (N. Schoenfeldt, Surface Active Ethylene Oxide Adducts, Pergamon Press 1969, page 81), whose disclosure is incorporated by reference herein, as well as the products of hydroformylation or hydrocarboxymethylation of terminal- and inner-positioned olefins and subsequent hydrogenation (N. Schoenfeldt, Surface Active Ethylene Oxide Adducts, Pergamon Press 1969, page 82), whose disclosure is incorporated by reference herein; ethylene glycol, propylene glycol, 1,3-propanediol, 1,3-butanediol, 1,4-butanediol, 1,2-hexanediol, 1,2-octanediol, 1,2-decanediol, 1,2-tetradecanediol, 1,2-hexadecanediol, 1,2-octadecanediol, 1,2-dodecanediol, etc.; aryl alcohols, such as 5-phenyl-1-decanol, 7-phenyl-1-dodecanol, $C_5$–$C_{11}$-phenyl-1-tetradecanol (i.e., the phenyl is on the 5- to 11-positions), $C_5$–$C_{11}$-phenyl-2-methyl-1-tridecanol, etc.; furthermore, alkyl phenols, such as 4-isononylphenol, 4-isooctylphenol, 4-n-dodecylphenol, 4-n-tridecylphenol, etc., mixtures of the two latter compounds, etc.

Aryl groups equivalent to the mentioned phenyl groups include phenyl rings substituted by methoxy, acetoxy, cyano, nitro, chloro, fluoro groups etc.

When R is alkyl, it preferably has 8–22 carbon atoms; as aralkyl, preferably it has 4–18 carbon atoms in the alkyl portion; as alkaryl, it preferably has 4–18 carbon atoms in the alkyl portion; as hydroxyalkyl, it preferably has 2–12 carbon atoms in the alkyl portion; and as (aryl)alkylene, it preferably has 4–18 carbon atoms in the alkyl portion. Most preferably, R is alkyl.

R can be hydroxyalkyl due to the failure of starting material diols to react completely with the epoxides.

Suitable R' and R" moieties of the compounds of this invention include those in the starting epoxy components of the formula

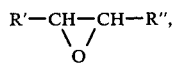

e.g., 1,2-epoxides of 10–22 carbon atoms, central-positioned epoxides of the same carbon atom number, as well as mixtures thereof.

Especially advantageous are epoxides of 10–16 carbon atoms.

Such epoxides include, for example, 1,2-epoxydecane, 1,2-epoxydodecane, 1,2-epoxytetradecane, 1,2-epoxyhexadecane, 1,2-epoxyoctadecane, 1,2-epoxyeicosane, 1,2-epoxydodecane/-tetradecane/-hexadecane as a mixture; the product of the reaction of a mixture of central-positioned olefins of 11–15 carbon atoms with a suitable percarboxylic acid, etc.

The quantitative ratios of hydroxyhydrocarbon, ethylene oxide, and epoxide with respect to one another should be such that the lipophilic proportion of the novel compounds of this invention is of an order of magnitude of 35–75% by weight, preferably 40–60% by weight, of the molecule, the remainder being hydrophilic. If the lipophilic value falls short of this lower limit, the solubility of the compounds in the oily phase can become so low that deposition occurs on the interface. The parts of the molecules derived from the hydroxyhydrocarbons and the epoxyalkanes

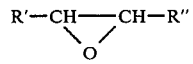

utilized as the reaction starting materials are considered lipophilic, whereas the segment derived from the ethylene oxide is, as usual, considered hydrophilic. A compound composed of 1 mole of 1-dodecanol, 20 moles of ethylene oxide, and 3 moles of 1,2-epoxytetradecane thus has a corresponding lipophilic:hydrophilic ratio of 48%:52%, and hence is within the preferred range.

In general, the HLB-values of the compounds of this invention are 5–13, preferably 8–12.

x is preferably 20–30 and y is preferably 1.3–3.

Preferred values of x and y are, of course, to be selected in accordance with the preferred component weight percentages mentioned above which, in turn, are determined in accordance with the requirements on hydrophilic/lipophilic characteristics.

Thus, in the process of this invention, the relative amounts of reactant materials are determined in accordance with the desired final values of x and y assuming complete reaction.

The molecular weights of the thus-prepared surface-active agents are generally in the range of 1,500 and 2,500 when using as starting materials the preferred primary alcohols of the fatty alkyl range of $C_8$–$C_{22}$ and the 1,2-epoxyalkanes of the same carbon atom range and when the preferred ratio between the lipophilic and hydrophilic proportion of the desired end product is maintained. If other special alcohols or epoxides are utilized for certain purposes, the molecular weights can, of course, lie markedly outside of the aforementioned range.

The reaction of the compound $R(OH)_z$ with ethylene oxide and thereafter with the epoxyalkane

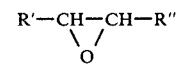

can be carried out in the presence of either a basic catalyst, such as sodium or potassium hydroxide, alcoholates of 1–4 carbon atoms, such as sodium methylate, sodium ethylate or potassium tert-butanolate at temperatures of 160°–230° C., preferably at 180°–210° C.; or an acidic catalyst, such as boron trifluoride or complex oxonium or carbenium salts, e.g., triethyloxonium tetrafluoroborate, at temperatures of 80°–160° C., preferably at 100°–140° C. A suitable amount of catalyst is the customary quantity of about 1–3% by weight, based on the amount of starting $R(OH)_z$ compound introduced into the reaction. Generally, the first stage of the reaction (addition of ethyleneoxide) is carried out at lower temperatures (150°–170° C. (base): 80°–90° C. (acid)) for 1–2 hours; and the second stage (epoxyalkane addition) at higher temperatures (160°–210° C. (base); 120°–140° C. (acid)) for 1.5–2.5 hours.

The reaction can be carried out under normal pressure, but a pressure in excess of normal by 0.5–3 atmospheres can be advantageously utilized. The techniques for achieving the block structure of the compounds of this invention are fully conventional, as are the reaction conditions and operations not described in detail herein. See, for example, U.S. Pat. No. 2 903 485, whose disclosure is incorporated by reference herein. In general, the reaction is completed to an extent of 100%.

It has now been found, surprisingly, that, in contrast to the prior art, the compounds of this invention exhibit completely unexpected properties. The members of this class of compounds are practically water-insoluble; accordingly, they do not possess a cloud point detectable by standard methods, and they cannot be grouped into the class of low-foaming detergent raw materials. Rather, the novel adducts of this invention show a pronounced solubility in nonpolar phases, such as, for example, paraffin oil.

Another unexpected property of the compounds of this invention resides in the fact that only very small concentrations thereof in an oil phase will lower the interfacial surface tension of the latter with respect to water to values of <1 mN/m. Compounds exhibiting such behavior are utilized as the moderating additive to strongly foaming tensides. Furthermore, they are suitable for use as an engine oil additive, since they suppress the foaming of such an oil during operation which is caused by the entrance of water and otherwise would reduce the desired lubricating effect. Also because of this property, another use of the compounds of this invention is as auxiliary emulsifying agents. This listing of fields of use is not, of course, meant to restrict the scope of this invention, but merely to explain some of the desirable advantages obtainable from the surprising behavior of the compounds of this invention.

As mentioned, the compounds of this invention show activity at very small concentrations, as low as 0.002% by weight; however, they will usually be employed in concentrations of 2–0.02%, especially 1–0.2% by weight in the above-mentioned uses. Consequently, formulations of detergent compositions, e.g., for dishwashers, are disclosed, e.g., in N. Schoenfeldt, Surface Active Ethylene Oxide Adducts, Pergamon Press 1969, page 424–441, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The examples which follow illustrate the methods for preparing the novel compounds of this invention and the surprising effects of the latter as compared to modified ethylene oxide addition compounds of the state of the art.

EXAMPLE 1

62.0 g (0.333 mol) of 1-dodecanol was reacted in the presence of 0.8 g of pulverized sodium hydroxide with 299.0 g (6.795 mol) of ethylene oxide at 160° C. Thereafter, 212.3 g (1.000 mol) of 1,2-epoxytetradecane was added dropwise and the mixture stirred at 160° C. After 2 hours, the epoxy content was 5.2%; after another 6 hours the epoxide had been used up. The values for the interfacial surface tension are indicated in No. 1 of Table 1. The polydiol content of the product was determined to be 0.1%.

EXAMPLE 2

72.5 g (0.250 mol) of "Alfol" 1620 was reacted in the presence of 1.0 g of pulverized sodium hydroxide with 241.0 g (5.477 mol) of ethylene oxide at 160° C. Then 117.2 g (0.750 mol) of 1,2-epoxydecane was added dropwise, and the mixture was stirred for 2 hours at 210° C.; after this time the epoxide had been consumed. The temperature, significantly higher than in experiment (1) thus leads to greatly reduced reaction periods. The polydiol content was 0.2%. The values for the interfacial surface tension are indicated in No. 6 of Table 1.

EXAMPLE 3

46.5 g (0.250 mol) of 1-dodecanol was reacted in the presence of 0.8 g of pulverized sodium hydroxide with 318 g (7.227 mol) of ethylene oxide and 106.2 g (0.500 mol) of 1,2-epoxytetradecane, analogously to Example 1. The product containing 0.1% polydiol showed, in a 2%- and 0.2%-solution in paraffin oil, crystalline deposits on the interface to the water; the interfacial surface tension of both solutions ranged at 1–2 mN/m. The high hydrophilic proportion of 68% is no longer within the preferred range and leads to a disturbance of the solution characteristic.

EXAMPLE 4

The following Table 1 indicates the values for the interfacial surface tension in the paraffin-oil/water system of oily solutions of tensides according to this invention at varying concentrations. The products employed were made from the aforementioned components analogously to Example 2. Additionally indicated, for comparison purposes, are the measured values for a tenside of analogous structure, but containing only one mole of added, 1,2-epoxyalkane; for a tert-butyl ether; for an ethoxylated fatty alcohol mixture; and for an ethylene oxide-propylene oxide adduct to nonylphenyl, utilized as a low-foaming tenside in dishwashing detergents.

EXAMPLE 5

37.2 g (0.200 mol) of 1-docecanol was combined with 0.5 ml of boron trifluoride etherate and reacted with 185 g (4.185 mol) of ethylene oxide at 80°–90° C. After the addition of another 0.6 ml of catalyst, 127.2 g (0.600 mol) of 1,2-epoxytetradecane was added dropwise at 90°–100° C. and the mixture was then stirred for one hour at 130° C.; thereafter, a content of free epoxide was no longer detectable. After the removal under vacuum of low-boiling compounds produced in a secondary reaction, a colorless, pasty product remained which contained per 1 mole of 1-dodecanol 16.7 moles of ethylene oxide and 3 moles of 1,2-epoxytetradecane in the form of the linear adduct. The polydiol content was 2.4%.

EXAMPLES 6–25

Table 2 contains further examples of the tensides of this invention, produced with varying starting alcohols, 1,2-epoxyalkanes, and catalysts. All products are water-insoluble and exhibit the above-mentioned effect on oil/water interfaces.

TABLE 1

Interfacial Surface Tensions at 20° C. Measured at Varying Concentrations of Tensides of This Invention in Paraffin Oil with Respect to Fully Demineralized Water

| No. | Alcohol Component | EO* | 1,2-Epoxy-alkane | Number* | Polydiol Content (%) | Interfacial Surface Tension (mN/m) at: | | | |
|---|---|---|---|---|---|---|---|---|---|
| | | | | | | 2% | 0.2% | 0.02% | 0.002% |
| 1 | 1-Dodecanol | 20 | $C_{14}H_{28}O$ (a) | 3 | 0.1 | <1 | <1 | 1.5 | 4 |
| 2 | 1-Dodecanol | 22.6 | $C_{14}H_{28}O$ (b) | 3 | 0.2 | <1 | <1 | <1 | 3.5 |
| 3 | Fatty alcohol $C_{10/12}$ | 17.5 | $C_{10}H_{20}O$ | 3 | 0.2 | <1 | <1 | 2 | 4.5 |
| 4 | Fatty alcohol $C_{10/12}$ | 21.9 | $C_{14}H_{28}O$ | 3 | 0.3 | <1 | <1 | <1 | 3 |
| 5 | Fatty alcohol $C_{10/12}$ | 25 | $C_{16}H_{32}O$ | 3 | 0.5 | <1 | <1 | <1 | 3 |
| 6 | Fatty alcohol $C_{16/20}$ | 21.9 | $C_{10}H_{20}O$ | 3 | 0.2 | <1 | <1 | <1 | 3.5 |
| 7 | Fatty alcohol $C_{16/20}$ | 31 | $C_{14}H_{28}O$ | 3 | 0.4 | <1 | <1 | <1 | 3 |
| 8 | Fatty alcohol $C_{16/20}$ | 31.5 | $C_{16}H_{32}O$ | 3 | 0.4 | <1 | <1 | <1 | 4.5 |
| Comp. | 1-Dodecanol | 20 | $C_{14}H_{28}O$ | 1 | 0.6 | 1.0 | 1.5 | 3.0 | — |
| " | Fatty alcohol $C_{16/18}$ | 6 | $t-C_4H_6-$ | 1 | — | 1.0 | 1.5 | 5.5 | — |

TABLE 1-continued

Interfacial Surface Tensions at 20° C. Measured at Varying Concentrations of Tensides of This Invention in Paraffin Oil with Respect to Fully Demineralized Water

| No. | Alcohol Component | EO* | 1,2-Epoxy-alkane | Number* | Polydiol Content (%) | Interfacial Surface Tension (mN/m) at: 2% | 0.2% | 0.02% | 0.002% |
|---|---|---|---|---|---|---|---|---|---|
| " | Nonylphenol | 9 | C₃H₆O | 10 | <3 | 2.5 (c) | — | — | — |

(a) 1,2-Epoxytetradecane added at 160° C.
(b) 1,2-Epoxytetradecane added at 210° C.
(c) 2% Solution in fully demineralized water.
*EO and Number respectively refer to the number of moles of EO and 1,2-epoxyalkane per mole of alcohol component.

TABLE 2

Tensides of This Invention Made from Various Starting Alcohols, Epoxides, and Catalysts

| Example | Alcohol Component | EO* | 1,2-Epoxyalkane | Number* | Polydiol Content (%) | Catalyst |
|---|---|---|---|---|---|---|
| 6 | Fatty alcohol C₁₀/₁₂ | 19 | hexadecane | 3 | 2.3 | BF₃ |
| 7 | Fatty alcohol C₁₀/₁₂ | 14 | decane | 3 | 1.1 | BF₃ |
| 8 | Fatty alcohol C₁₆/₂₀ | 16 | decane | 3 | 1.1 | BF₃ |
| 9 | Fatty alcohol C₁₆/₂₀ | 17 | tetradecane | 3 | 2.1 | BF₃ |
| 10 | Fatty alcohol C₁₆/₂₀ | 20 | hexadecane | 3 | 1.6 | BF₃ |
| 11 | Nonylphenol | 13 | hexadecane | 1.3 | 0.1 | NaOH |
| 12 | Nonylphenol | 12 | tetradecane | 1.3 | 0.2 | NaOH |
| 13 | Nonylphenol | 11 | decane | 1.3 | 0.1 | NaOH |
| 14 | Nonylphenol | 11 | tetradecane | 2 | 0.1 | NaOH |
| 15 | Nonylphenol | 22 | tetradecane | 3 | 0.2 | NaOH |
| 16 | Nonylphenol | 16 | decane | 4 | 0.3 | NaOH |
| 17 | Nonylphenol | 16 | decane | 2 | 0.4 | NaOH |
| 18 | Nonylphenol | 21 | decane | 3 | 0.2 | BF₃ |
| 19 | Nonylphenol | 20 | decane | 3 | 0.3 | NaOH |
| 20 | Nonylphenol | 20 | hexadecane | 3 | 0.4 | NaOH |
| 21 | Nonylphenol | 26 | hexadecane | 3 | 0.5 | NaOH |
| 22 | 2-Ethylhexanol | 30 | tetradecane | 3 | 0.4 | NaOH |
| 23 | n-Butanol | 25 | tetradecane | 3 | 1.2 | NaOH |
| 24 | 1,2-Decanediol | 10 | decane | 2 | 0.2 | NaOH |
| 25 | 1,4-Butanediol | 13 | hexadecane | 2 | 0.3 | NaOH |

*EO and Number respectively refer to the number of moles of EO and 1,2-epoxyalkane per mole of alcohol component.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

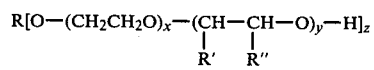

wherein
z is 1 or 2,
R is, for z=1, alkyl, aralkyl, or alkylaryl, each of 8–22 carbon atoms in the alkyl chain, or hydroxyalkyl of 2–22 carbon atoms, and, for z=2, alkylene or arylalkylene, each of 4–18 carbon atoms in the alkyl chain, wherein, aryl in each case is phenyl or phenyl substituted by methoxy, acetoxy, cyano, nitro, chloro or fluoro,
R' and R" each independently is hydrogen or C₁–C₂₀-alkyl wherein R' and R" are not simultaneously hydrogen and R' and R" together have a total of 8–20 carbon atoms,
x is 10–40, and
y is 1.2–5,
said compound being essentially water insoluble, possessing essentially no cloud point and being effective to lower the interfacial surface tension of an oil phase with respect to water when present in the oil phase in a small concentration.

2. A compound of claim 1, wherein x is 20–30 and y ix 1.3–3.

3. A compound of claim 1, wherein R is straight-chain alkyl.

4. A compound of claim 1, wherein one of R' and R" is H and the other is straight-chain alkyl.

5. A process for preparing a compound of claim 1, comprising reacting a compound R(OH)z in the presence of a basic or acidic catalyst first with ethylene oxide and then with an epoxyalkane of the formula

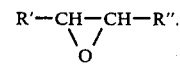

6. A process of claim 5, wherein R(OH)z is a fatty alcohol of 8–22 carbon atoms or a mixture thereof.

7. A process of claim 6, wherein the epoxyalkane is a 1,2-epoxyalkane of the fatty alkyl range of 10–22 carbon atoms, or a mixture thereof.

8. A process of claim 6, wherein a basic catalyst is used and the reaction temperature is 160°–230° C.

9. A process of claim 6, wherein an acidic catalyst is used and the reaction temperature is 80°–160° C.

10. A detergent composition comprising an amount of a compound of claim 1 effective to lower the interfacial surface tension of an oily phase with respect to water and an adjuvant conventional in detergent compositions.

11. A method of lowering the surface tension of an oily phase with respect to water which comprises incorporating in the oily phase an amount of a compound of claim 1 effective to lower said surface tension.

* * * * *